United States Patent
Caracci et al.

(10) Patent No.: US 7,057,720 B2
(45) Date of Patent: Jun. 6, 2006

(54) OPTICAL INTERROGATION SYSTEM AND METHOD FOR USING SAME

(75) Inventors: Stephen J. Caracci, Elmira, NY (US); Norman H. Fontaine, Painted Post, NY (US)

(73) Assignee: Corning Incorporated, Corning, NY (US)

( * ) Notice: Subject to any disclaimer, the term of this patent is extended or adjusted under 35 U.S.C. 154(b) by 223 days.

(21) Appl. No.: 10/602,304

(22) Filed: Jun. 24, 2003

(65) Prior Publication Data

US 2004/0263841 A1 Dec. 30, 2004

(51) Int. Cl.
*G01J 3/00* (2006.01)

(52) U.S. Cl. ....................................... 356/300
(58) Field of Classification Search ................ 356/300, 356/328, 334; 359/641
See application file for complete search history.

(56) References Cited

U.S. PATENT DOCUMENTS

| | | | |
|---|---|---|---|
| 4,815,843 A | 3/1989 | Tiefenthaler et al. | 356/128 |
| 5,071,248 A | 12/1991 | Tiefenthaler et al. | 356/128 |
| 5,313,264 A | 5/1994 | Ivarsson et al. | 356/73 |
| 5,479,260 A | 12/1995 | Fattinger | 356/361 |
| 5,738,825 A | 4/1998 | Rudigier et al. | 422/82.11 |
| 6,100,991 A | 8/2000 | Challener | 356/445 |
| 6,346,376 B1 | 2/2002 | Sigrist et al. | 435/5 |
| 6,429,022 B1 | 8/2002 | Kunz et al. | 436/164 |
| 6,570,657 B1 * | 5/2003 | Hoppe et al. | 356/445 |
| 6,665,069 B1 * | 12/2003 | Permogorov et al. | 356/328 |
| 6,785,433 B1 | 8/2004 | Tiefenthaler | 385/12 |
| 2001/0021026 A1 | 9/2001 | Liu | 356/601 |
| 2001/0026943 A1 | 10/2001 | Dickopf et al. | 436/164 |
| 2001/0046050 A1 * | 11/2001 | Hoyt | 356/417 |
| 2002/0001085 A1 | 1/2002 | Dickopf et al. | 356/445 |
| 2002/0109100 A1 | 8/2002 | Jackson, III et al. | 250/458.1 |
| 2002/0127565 A1 | 9/2002 | Cunningham et al. | 435/6 |
| 2002/0168295 A1 | 11/2002 | Cunningham et al. | 422/82.05 |
| 2003/0007896 A1 | 1/2003 | Tiefenthaler | 422/91 |
| 2003/0017580 A1 | 1/2003 | Cunningham et al. | 435/287.2 |
| 2003/0017581 A1 | 1/2003 | Li et al. | 435/287.2 |
| 2003/0026891 A1 | 2/2003 | Qiu et al. | 427/58 |

(Continued)

FOREIGN PATENT DOCUMENTS

EP 0 202 021 11/1986

(Continued)

OTHER PUBLICATIONS

A. Bradenburg et al., "Grating couplers as chemical sensors: a new optical configuration", Sensors and Actuators B, vol. 17, 1993, pp. 35-40.

(Continued)

*Primary Examiner*—Gregory J. Toatley, Jr.
*Assistant Examiner*—Kara Geisel
(74) *Attorney, Agent, or Firm*—William J. Tucker, Esq.; Thomas R. Beall (57) ABSTRACT

An optical interrogation system and method are described herein that are capable of generating light beams that have desired optical properties which are directed towards a specimen array. In one embodiment, the optical interrogation system includes a light source, a diffractive element and a collimating optic (e.g., simple lens(es), f-θ lens(es), segmented mirror, fiber array). The light source emits a light beam to the diffractive optic which receives the light beam and outputs an array of light beams to the collimating optic. The collimating optic receives and conditions the light beams emitted from the diffractive optic and then outputs the conditioned light beams which have desired optical properties towards a specimen array. Several other embodiments of the optical interrogation system are also described herein.

45 Claims, 7 Drawing Sheets

U.S. PATENT DOCUMENTS

| | | | |
|---|---|---|---|
| 2003/0027327 A1 | 2/2003 | Cunningham et al. | ... 435/287.2 |
| 2003/0027328 A1 | 2/2003 | Cunningham et al. | ... 435/287.2 |
| 2003/0032039 A1 | 2/2003 | Cunningham et al. | ......... 435/6 |
| 2003/0059855 A1 | 3/2003 | Cunningham et al. | ....... 435/7.9 |
| 2003/0068657 A1 | 4/2003 | Lin et al. | ...................... 435/7.9 |
| 2003/0077660 A1 | 4/2003 | Pien et al. | ................... 435/7.1 |
| 2003/0092075 A1 | 5/2003 | Pepper | ....................... 435/7.9 |
| 2003/0113766 A1 | 6/2003 | Pepper et al. | ................... 435/6 |
| 2003/0128437 A1* | 7/2003 | Sato et al. | ................. 359/641 |
| 2003/0133640 A1 | 7/2003 | Tiefenthaler | ................ 385/12 |
| 2003/0160957 A1* | 8/2003 | Oldham et al. | ............. 356/317 |
| 2003/0218746 A1* | 11/2003 | Sampas | ....................... 356/318 |
| 2004/0132172 A1 | 7/2004 | Cunningham et al. | ... 435/287.2 |
| 2004/0132214 A1 | 7/2004 | Lin et al. | ................... 436/518 |
| 2004/0151626 A1 | 8/2004 | Cunningham et al. | ........ 422/58 |
| 2004/0223881 A1 | 11/2004 | Cunningham et al. | ... 422/82.05 |

FOREIGN PATENT DOCUMENTS

| | | |
|---|---|---|
| EP | 1 271 219 | 1/2003 |
| WO | WO 90/09560 | 8/1990 |

OTHER PUBLICATIONS

R. Horváth et al., "Demonstration of reverse symmetry waveguide sensing in aqueous solutions", Applied Physics Letters, vol. 81, No. 12, Sep. 16, 2002, pp. 2166-2168.

W.A. Challener et al., "A multilayer grating-based evanescent wave sensing technique", Sensors and Actuators B, vol. 71, 2000, pp. 42-46.

F.F. Bier et al., "Real-time measurement of nucleic-acid hybridization using evanescent-wave sensors: steps toward the genosensor", Sensors and Actuators B., vols. 38-39, 1997, pp. 78-82.

* cited by examiner

OPTICAL INTERROGATION SYSTEM AND METHOD FOR USING SAME

BACKGROUND OF THE INVENTION

1. Field of the Invention

The present invention relates to an optical interrogation system and method capable of generating light beams that have desired optical properties which are directed towards a specimen array.

2. Description of Related Art

One of the most significant challenges for manufacturers of optical interrogation systems is to design an efficient and cost effective system that is capable of illuminating an array of specimens with light beams that have desired optical qualities like the proper spatial, angular, and power profiles. This problem becomes even more acute as the dimensions and the density of the array of specimens increase. In the past, optical interrogation systems have used lenslet arrays, fiber arrays, "flood illumination" and scanning methods to address this problem. Unfortunately, these systems are often costly to construct and difficult to use because it is hard to generate light beams that have the appropriate optical character and which align with all of the specimens. Another reason why it is difficult to design efficient and cost effective optical interrogation systems is because the specifications for the system design often have conflicting requirements. The following is a list of some of these different scanning and non-scanning applications and their associated requirements:

Application—high specimen density.
   The optical interrogation system will have to make many moves to scan the entire specimen array.
   The optical interrogation system will have to incorporate a plurality of identical optical components which are precisely machined and positioned.
Application—large specimen array area.
   The optical interrogation system should have a large scan range.
   The optical interrogation system should be able to perform high-speed moves between specimens.
Application—precise positioning and re-positioning of the light beam and/or specimen array.
   The optical interrogation system should have a small step size resolution.
   The optical interrogation system should have precisely machined motion hardware and optics.
   The optical interrogation system should have encoder feedback hardware.
   The optical interrogation system should move slowly to allow precise alignment and re-alignment to each specimen.
Application—maximum integration time at each specimen.
   The optical interrogation system should be able to maintain a light beam at each specimen location for long data integration periods.
Application—rapid repetition of the scan of the specimen array.
   The optical interrogation system should be able to perform high-speed moves between specimens.
   The optical interrogation system should have a short interrogation time at each specimen.
Application—precisely controlled beam intensity, spatial profile, and angular profile characteristics at each specimen.

The optical system requires many optical components with precise optical characteristics and positions.

One optical interrogation system that can generate multiple light beams while using few or no moving parts incorporates an array of optical components such as a lenslet or fiber array. However, these types of optical interrogation systems have several drawbacks. First, these systems require the use of a number of precisely positioned and designed optical elements in order to convey light beams to one or more lenslets, fibers, and/or specimens. Another drawback of these types of optical interrogation systems is that they require the use of additional components to ensure that the light beams have the appropriate optical power and intensity profile when they are introduced into each lenslet, fiber or specimen.

Another type of optical interrogation system could incorporate a device such as a beam expander that "flood illuminates" the specimen array. However, these types of optical interrogation systems have several drawbacks including (1) loss of optical power when light beams fall outside the lenslet elements, fibers or the specimen interrogation region; (2) increased measurement noise and error due to light beams that scatter from undesirable regions of the lenslet, fiber or specimen array; and (3) difficulty of ensuring the proper illumination including intensity, numerical aperture, etc. of all elements in the array of lenslets, fibers or specimens.

Yet another type of optical interrogation could rely on various scanning methods to illuminate the specimens. However, these scanning systems have several drawbacks because they require the use of precise alignment hardware and software and they do not allow for long integration times at each specimen. Accordingly, there is a need for a new optical interrogation system that addresses the aforementioned shortcomings and other shortcomings in the traditional optical interrogation systems. These needs and other needs are satisfied by the optical interrogation system and method of the present invention.

BRIEF DESCRIPTION OF THE INVENTION

The present invention includes an optical interrogation system and method capable of generating light beams that have desired optical properties which are directed towards a specimen array. In one embodiment, the optical interrogation system includes a light source, a diffractive element, and a collimating optic (e.g., simple lens(es), f-θ lens(es), segmented mirror). The light source emits a light beam to the diffractive optic which receives the light beam and outputs an array of light beams to the collimating optic. The collimating optic receives and conditions the light beams emitted from the diffractive optic and then outputs the conditioned light beams which have desired optical properties towards a specimen array. Several other embodiments of the optical interrogation system are also described herein. It should also be noted that the optical interrogation system can be used in a wide variety of optical signal transduction methods (e.g., IR absorption, FTIR and other vibrational spectroscopies) that may be used to interrogate and receive information about the specimen array.

BRIEF DESCRIPTION OF THE DRAWINGS

A more complete understanding of the present invention may be had by reference to the following detailed description when taken in conjunction with the accompanying drawings wherein.

DETAILED DESCRIPTION OF THE DRAWINGS

Referring to FIGS. 1–10, there are disclosed in accordance with the present invention nine embodiments of an optical interrogation system 100 and method 1000 for using the optical interrogation system 100 to interrogate one or more specimens in a specimen array. It should be readily appreciated by those skilled in the art that the optical interrogation system 100 can be used to interrogate a specimen array to determine whether or not a biological substance such as a cell, molecule, protein, drug, chemical compound, nucleic acid, peptide or carbohydrate is present within anyone of the specimens in the specimen array. The optical interrogation system 100 can also be used to perform other label or label-free studies such as photoluminescence assays, fluorescence assays, scattering assays, absorbance assays, cell migration assays, drug permeability assays, drug solubility studies, virus detection studies and protein secretion studies. Accordingly, the optical interrogation system 100 and method 1000 and their possible uses should not be construed in a limited manner.

Figure 1A:
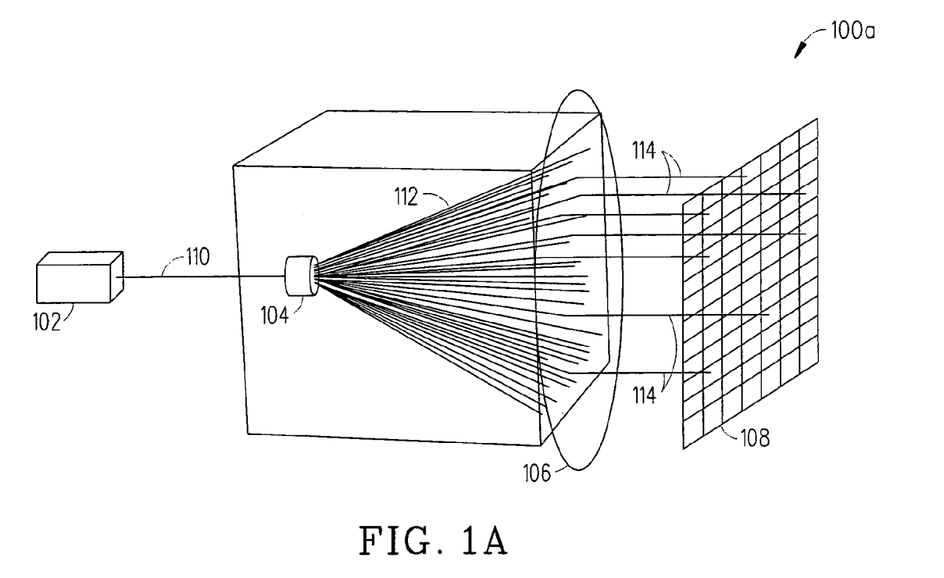
FIG. 1A is a diagram of a first embodiment of an optical interrogation system that uses a light source, a diffractive optic and a collimating optic to illuminate a specimen array in accordance with the present invention.

Referring to FIG. 1A, there is shown a diagram of a first embodiment of the optical interrogation system 100a. The optical interrogation system 100a includes a light source 102, a diffractive optic 104 and a collimating optic 106 which are used to illuminate a specimen array 108. As shown, the light source 102 outputs a light beam 110 towards the diffractive optic 104. The diffractive optic 104 receives the light beam 110 and outputs an array of light beams 112 which have a desired spatial and angular intensity distribution towards the collimating optic 106. The collimating optic 106 receives the light beams 112 and outputs a conditioned array of light beams 114 which have desired inter-beam separations and angles towards the specimen array 108. A more detailed discussion about each of these components is described below in the order in which they appear in the optical path.

The light source 102 can be any mechanism capable of producing light 110 suitable for use in an optical assay, such as a photoluminescence assay, a scattering assay and an absorbance assay. For example, the light source 102 can be a laser, arc lamp, incandescent lamp, fluorescent lamp, electroluminescent device, laser diode, and light-emitting diode (LED). The light source 102 may have one or more illumination modes, including continuous or time-varying modes such as a pulsed laser, swept wavelength, or swept bandpass. In addition, the light source 102 may produce a coherent or incoherent and/or polarized or unpolarized light beam 110.

The diffractive optic 104 can be any mechanism capable of converting the input light beam 110 into the array of light beams 112 that have a preselected spatial and angular intensity pattern. For example, the diffractive optic 104 can be a diffractive (e.g., binary) optical element that contains a glass, plastic and/or fused silica chip designed and patterned by holography, photolithography, scribing, molding, and/or other methods to create a predefined array of light beams 112 from incident light 110.

The collimating optic 106 can be any mechanism capable of conditioning the array of light beams 112 so that they have predetermined optical properties such as desired inter-beam separations and angles before they are directed towards the specimen array 108. For example, the collimating optic 106 can be a simple lens, a series of simple lenses, a f-θ lens, a parabolic mirror, a segmented mirror 206 (see FIG. 2), a refracting "lens" that includes a set of precisely placed and angled refracting wedges, a fiber array or lenslet array 306 (see FIG. 3) or a combined fiber array/lenslet array 406 (see FIG. 4). While a simple lens 106 can be used to direct the array of light beams 114, the angle of incidence of these light beams 114 may not be sufficiently uniform across the specimen array 108 due to optical aberrations. To achieve uniform incidence angles for the array of light beams 114 across the specimen array 108, a f-θ lens 106 could be used. While a parabolic mirror 106 could be used to collimate a uniform-angled array of light beams 112 received from the diffractive optic 104, the inter-beam separation and beamlet character may not be consistent across the collimated light beams 114. To correct this problem, the parabolic mirror 106 may be replaced with a segmented mirror 206 which is described in greater detail below with respect to FIG. 2.

The specimen array 108 can be any mechanism capable of supporting a sample and particularly a plurality of samples at a corresponding plurality of sample sites for analysis. For example, the specimen array 108 can be a microplate, PCR plate, cell culture plate, biochip, hybridization chamber, chromatography plate or microscope slide. If the specimen array 108 is a microplate then sensors (e.g., grating based waveguide sensors) can be incorporated within the bottom of wells which are illuminated by light beams 114 emitted from the collimating optic 106. For example, the collimating optic 106 can be designed to direct light beams 114 into the wells in a 24, 96, 384 or 1536 well microplate 108 (for example). A more detailed discussion about how a sensor can be incorporated within the bottom of a well in a microplate is provided in U.S. Pat. No. 5,738,825 the contents of which are incorporated by reference herein.

Although it is not shown in FIG. 1A, the collimating optic 106 may not be required if the specimen array 108 is curved with the appropriate radius centered at the diffractive optic 104. It should also be appreciated that a beam splitting optic (not shown) could be placed between the array of beams 114 and the specimen array 108 to allow near normal incidence illumination and signal detection, if it is needed. Moreover, it should be appreciated that the entire specimen array 108, or sections of the specimen array 108, can be illuminated by one or more sets of light sources 102 and optics 104 and 106. If a sub-section of an array is illuminated by this method an advantage is gained because the number of moves in a scanning system can be reduced by a factor corresponding to the number of beamlets in the array.

Figure 1B:
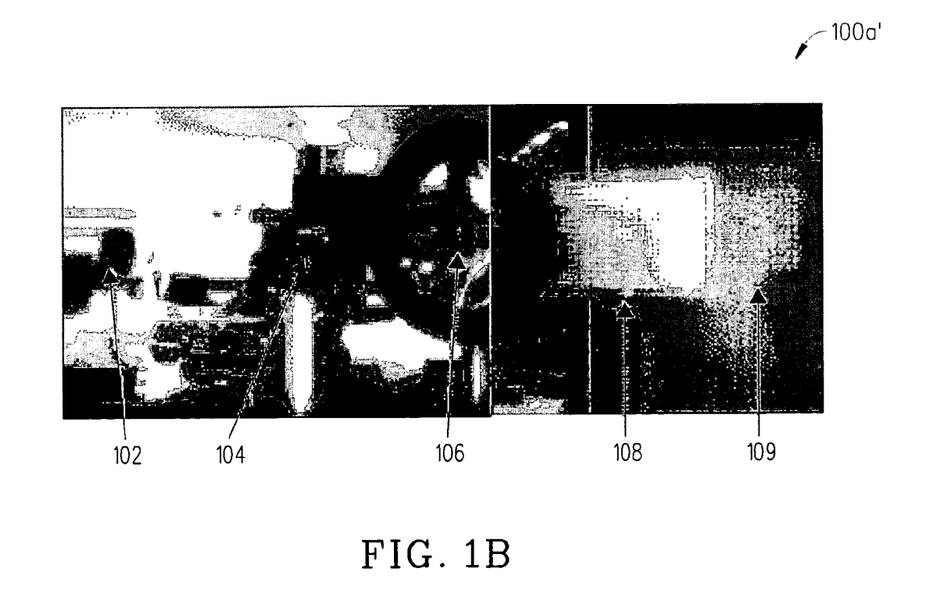
FIG. 1B is a photograph of an exemplary optical interrogation system similar to the one shown in FIG. 1A that uses a He/Ne laser, two spot-to-linear-array diffractive optics that were oriented perpendicular to each other (generating a 2-D grid of beamlets), and a plano-convex collimating lens to illuminate a 384 micro-array well plate in accordance with the present invention.

Referring to FIG. 1B, there is a photograph of an exemplary optical interrogation system 100a' that uses a He/Ne laser 102, two spot-to-linear-array diffractive optics 104 and a plano-convex collimating optic 106 to illuminate a 384 micro-array well plate 108. In this example, the light source 102 is a He/Ne laser 102 and the two diffractive optics 104 are 11-spot diffractive optics 104 oriented with perpendicular fan angles which generate an array of 121-light beams 112 that have 1.42 degrees separating the beams 112. The collimating optic 106 is a 3" diameter, 175 focal length plano-convex collimating optic 106 that can generate an array of beams 114 with 4.5 mm separation between each beam 114. The specimen array 108 is a 384 micro-array well plate 108 that has a 4.5 mm separation between the centers of the wells. And, each well has a clear aperture that is approximately 2.5 mm ×2.5 mm. The photograph also illustrates at numeral 109 a 11×11 grid of spots that were created after each individual light beam 114 passed cleanly through the clear aperture of each well in the 384 micro-array plate 108.

Figure 2:
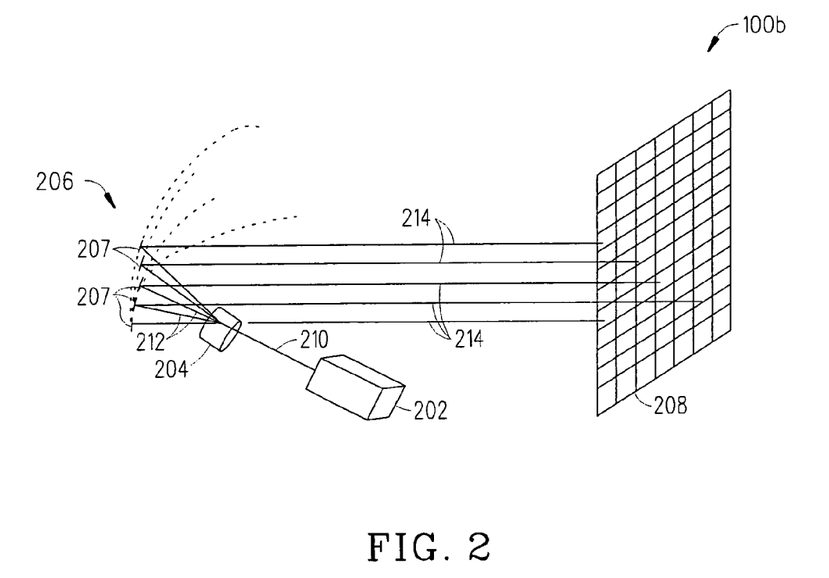
FIG. 2 is a diagram of a second embodiment of an optical interrogation system that uses a light source, a diffractive optic and a collimating optic configured as segmented mirror to illuminate a specimen array in accordance with the present invention.

Referring to FIG. 2, there is a diagram of a second embodiment of the optical interrogation system 100b. The optical interrogation system 100b includes a light source 202, a diffractive optic 204 and a segmented mirror 206 which are used to illuminate a specimen array 208. As shown, the light source 202 outputs a light beam 210 towards the diffractive optic 204. The diffractive optic 204 receives the light beam 210 and outputs an array of light beams 212 which have desired spatial and angular intensity distribution towards the segmented mirror 206. The segmented mirror 206 receives the light beams 212 and then reflects a collimated array of light beams 214 towards the specimen array 208. The segmented mirror 206 has an optical surface defined by a series of flat mirrors 207 (only five shown) which enables the collimated light beams 214 to have uniform inter-beam separations when the collimated light beams 214 are in planes that are parallel to the plane of the specimen array 208.

As can be seen, it is possible that the segmented mirror 206 can block some of the collimated light beams 214. To prevent the blocking of collimated light beams 214, the segmented mirror 206 may be located in a different axis with respect to the diffraction optic 204. To avoid repetition, the common components between the first and second embodiments of the optical interrogation system 100a and 100b such as the light source 102 and 202 and the diffractive optic 104 and 204 are not described in detail here since each of these components have similar structures and functionalities.

Figure 3:
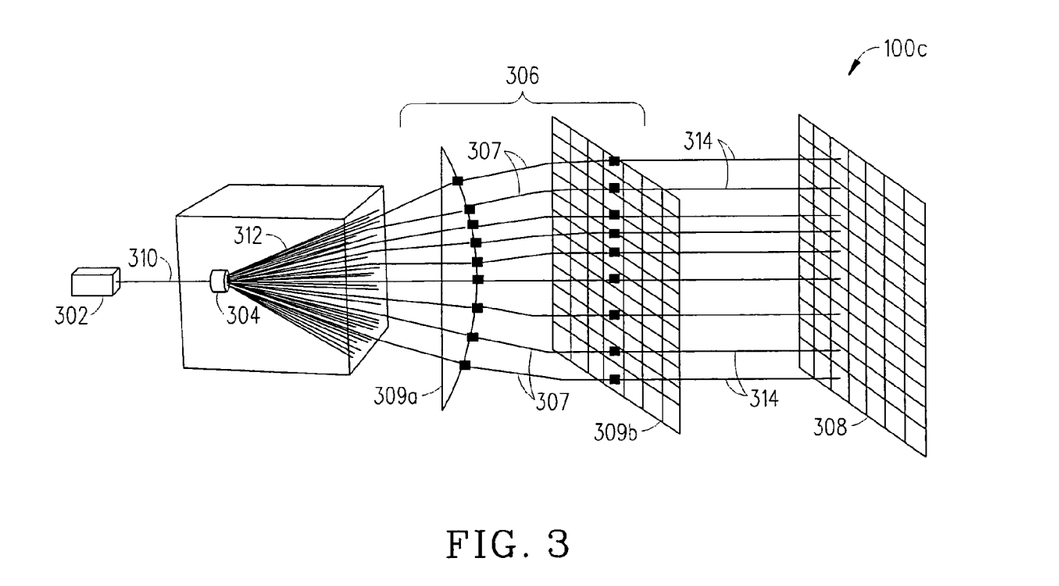
FIG. 3 is a diagram of a third embodiment of an optical interrogation system that uses a light source, a diffractive optic, and a collimating optic configured as fiber optics array to illuminate a specimen array in accordance with the present invention.

Referring to FIG. 3, there is a diagram of a third embodiment of the optical interrogation system 100c. The optical interrogation system 100c includes a light source 302, a diffractive optic 304 and a fiber array 306 which are used to illuminate a specimen array 308. As shown, the light source 302 outputs a light beam 310 towards the diffractive optic 304. The diffractive optic 304 receives the light beam 310 and outputs an array of light beams 312 which have a desired spatial and angular intensity distribution towards the fiber array 306. The fiber array 306 is made from an array of fibers 307 each of which has one end arranged on a sphere 309a and another end arranged on a grid 309b. The sphere 309a receives the light beams 312 and the fibers 307 re-condition the light beams 312 and then the conditioned light beams 314 are output from the grid 309b towards the specimen array 308. As shown, the fibers 307 may be arranged on the circumference of the sphere 309a whose optical center lies at the location of the diffractive optic 304. Alternatively, the fibers 307 may be arranged in a planar fashion instead of on the circumference of the sphere 309a. The fiber array 306 may be used if it is necessary to individually re-condition the optical character of each light beam 312 emitted from the diffractive optic 304. In another embodiment, a lenslet array (not shown) may be used instead of the fiber array 306 to alter the optical character of each light beam 312 into a desired form and then direct the re-conditioned light beams 314 toward the specimen array 308.

Figure 4:
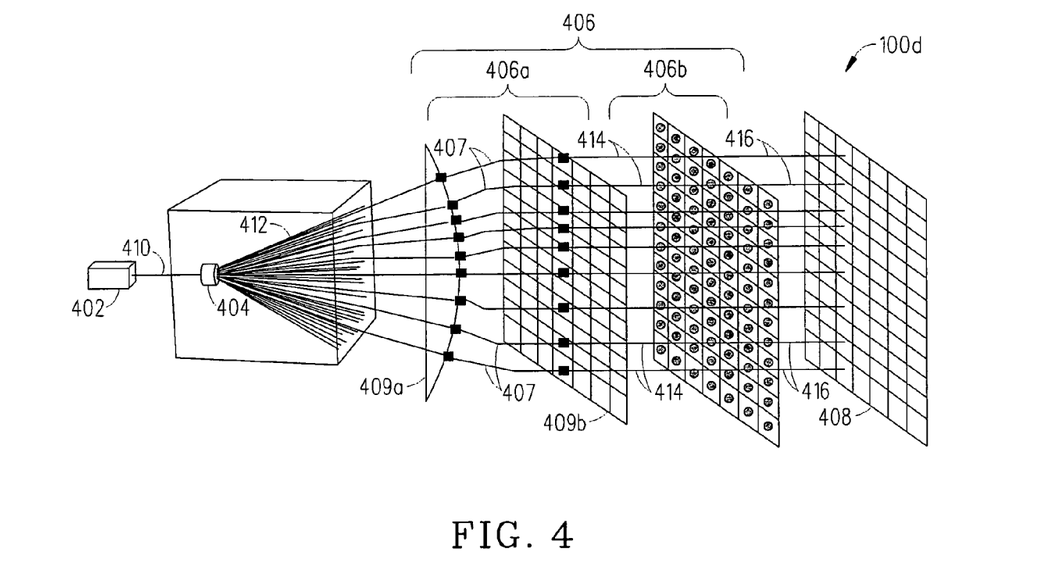
FIG. 4 is a diagram of a fourth embodiment of an optical interrogation system that uses a light source, a diffractive optic, and a collimating optic configured as a combined fiber optics array/lenslet array to illuminate a specimen array in accordance with the present invention.

Referring to FIG. 4, there is a diagram of a fourth embodiment of the optical interrogation system 100d. The optical interrogation system 100d includes a light source 402, a diffractive optic 404 and a combined fiber array/lenslet array 406 which are used to illuminate a specimen array 408. As shown, the light source 402 outputs a light beam 410 towards the diffractive optic 404. The diffractive optic 404 receives the light beam 410 and outputs an array of light beams 412 which have a desired spatial and angular intensity distribution towards the fiber array 406a. The fiber array 406a is made from an array of fibers 407 each of which has one end arranged on a sphere 409a and another end arranged on a grid 409b. The sphere 406a receives the light beams 412 and the fibers 407 re-condition the light beams 412 and then the conditioned light beams 314 are output from the grid 409b towards the lenslet array 406b. The lenslet array 406b further conditions the light beams 414 and directs the conditioned light beams 416 towards the specimen array 408. As shown, the fibers 407 may be arranged on the circumference of the sphere 409a whose optical center lies at the location of the diffractive optic 404. Alternatively, the fibers 407 may be arranged in a planar fashion instead of on a circumference of the sphere 409a. The combined fiber array/lenslet array 406 may be used if it is necessary to individually re-condition the optical character of each light beam 412 output from the diffractive optic 404. In another embodiment, one or more fiber arrays 406a and/or lenslet arrays 406b may be used to condition light beams 412 before they reach the specimen array 408.

Figure 5:
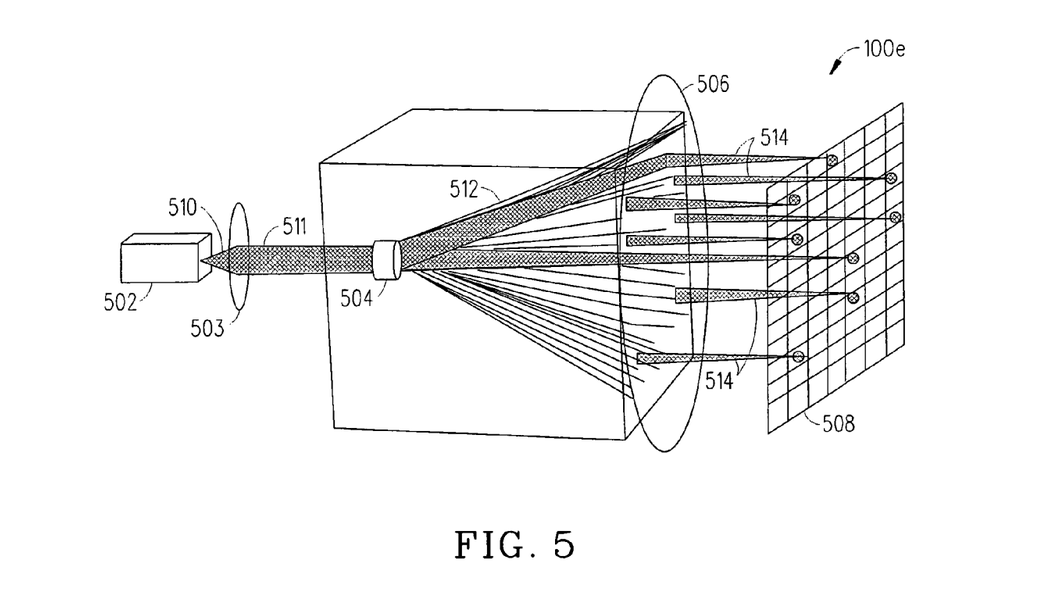
FIG. 5 is a diagram of a fifth embodiment of an optical interrogation system that uses a light source, a beamlet re-conditioning optic, a diffractive optic and a collimating optic to illuminate each specimen in a specimen array with the a desired spot size and numerical aperture in accordance with the present invention.

Referring to FIG. 5, there is a diagram of a fifth embodiment of the optical interrogation system 100e. The optical interrogation system 100e is similar to the first embodiment except that this optical interrogation system 100e includes a re-conditioning optic 503 which was not present in the first embodiment. To avoid repetition, the common components between the first and fifth embodiments of the optical interrogation system 100a and 100e such as the light source 102 and 502, the diffractive optic 104 and 504 and the collimating optic 106 and 506 are not described in detail below since each of these components have similar structures and functionalities.

The optical interrogation system 100e includes a light source 502, a re-conditioning optic 503, a diffractive optic 504 and a collimating optic 506 which are used to illuminate the specimen array 508. In this embodiment, the light source 502 outputs a light beam 510 towards the re-conditioning optic 503. The re-conditioning optic 503 receives the light beam 510 and outputs a re-conditioned light beam 511 towards the diffractive optic 504. The diffractive optic 504 receives the re-conditioned light beam 511 and outputs an array of light beams 512 which have a desired spatial and angular intensity distribution towards the collimating optic 506. The collimating optic 506 receives the light beams 512 and then outputs conditioned light beams 514 which have desired inter-beam separations and angles towards the specimen array 508.

The re-conditioning optic 503 allows one to re-condition the spot diameters and numerical apertures of each light beam 514 that impinges the plane of the specimen array 508. It is important to control the numerical aperture of each light beam 514 as well as the angle of incidence of each light beam 514 that is directed towards the specimen array 508 to ensure the proper functions and precise measurements when waveguide grating sensors and fluorescence sensors are arranged in the specimen array 508. Moreover, the re-conditioning optic 503 enables one to generate light beams 514 that have uniform optical interrogation properties across the entire specimen array 508 which helps ensure that the response of a particular sensor is not influenced by its location in the specimen array 508.

Figure 6:
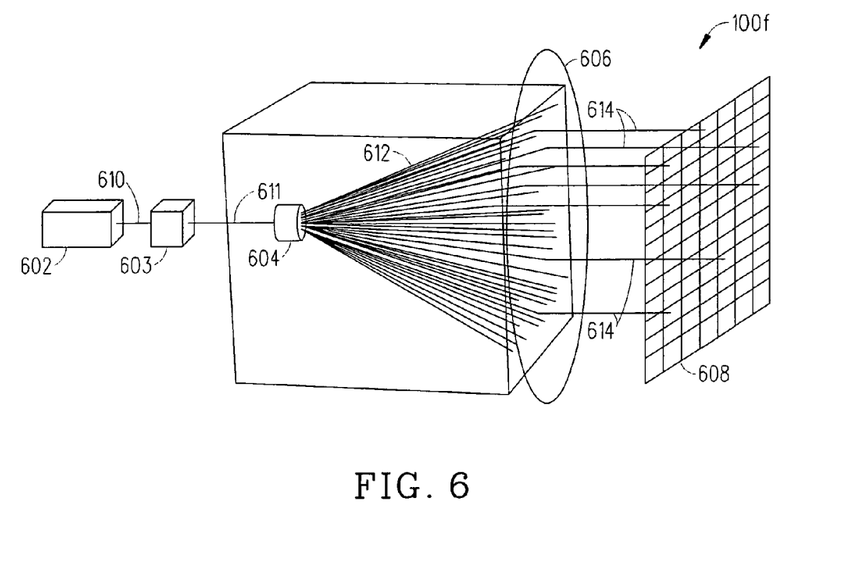
FIG. 6 is a diagram of a sixth embodiment of an optical interrogation system that uses a light source, a wavelength tunable filter, a diffractive optic and a collimating optic to illuminate a specimen array in accordance with the present invention.

Referring to FIG. 6, there is a diagram of a sixth embodiment of the optical interrogation system 100f. The optical interrogation system 100f is similar to the first embodiment except that this optical interrogation system 100f includes a wavelength tunable filter 603 which was not present in the first embodiment. To avoid repetition, the common components between the first and sixth embodiments of the optical interrogation system 100a and 100f such as the light source 102 and 602, the diffractive optic 104 and 604 and the collimating optic 106 and 606 are not described in detail below since each of these components have similar structures and functionalities.

The optical interrogation system 100f includes a light source 602, a wavelength tunable filter 603, a diffractive optic 604 and a collimating optic 606 which are used to illuminate the specimen array 608. As shown, the light source 602 outputs a light beam 610 towards the wavelength tunable filter 603. The wavelength tunable filter 603 receives the light beam 610 and outputs a filtered light beam 611 that has a frequency within a desired bandpass towards the diffractive optic 604. The diffractive optic 604 receives the filtered light beam 611 and outputs an array of light beams 612 which have a desired spatial and angular intensity distribution towards the collimating optic 606. The collimating optic 606 receives the light beams 612 and outputs conditioned light beams 614 which have desired inter-beam separations and angles towards the specimen array 608.

The wavelength tunable filter 603 enables one to scan the specimen array 608 with light beams 614 that have a desired wavelength. Thus, the wavelength tunable filter 603 enables the wavelength interrogation of the specimen array 608 using light beams 614 that have desired optical qualities at each specimen and does not require the use of expensive spectrographic and signal collection equipment. Since the diffractive optic 604 has a design wavelength bandpass typically specified at ~35 nm, the wavelength tunable filter 603 can be tuned only over a finite range of wavelengths before the beam quality of the light beams 614 begins to degrade at the specimen array 608. However, since the light beam 611 inputted into the diffractive optic 604 does not need to be precisely aligned to the diffractive optic 604 to create the fan of light beams 612 this enables one to use multiple diffractive optics 604. The use of multiple diffractive optics 604 that can be switched or moved with low precision allows one to interrogate the specimen array 608 with a greater range of wavelengths than would be possible with a single diffractive optic 604.

Those skilled in the art will appreciate that traditional spectrographic equipment and optical interrogation systems typically allows the signals from only about 10–20 specimens (or less) to be sampled at any one time. This forces the use of a scanning or multiplexing scheme to receive the light beams from the specimen array and to switch the light beam from each specimen to the input of the spectrographic equipment. However, the optical interrogation system 100f which includes the wavelength tunable filter 603 and diffractive optic 604 at the launch end enables one to use less expensive and more parallel detection schemes such as a photodiode arrays or CCDs. Because one axis of the CCD or photodiode array would not need to be used as a wavelength detection axis, the signals from a greater density of sensors in the specimen array 608 can be directed onto the CCD or detector array. This reduces the number of detectors and optics that must be used at the optical receive end of the optical interrogation system 100f. For a more detailed discussion about some of the different types of detectors that can be used in the present invention reference is made to the description associated with FIG. 7B–7C.

Figure 7A:
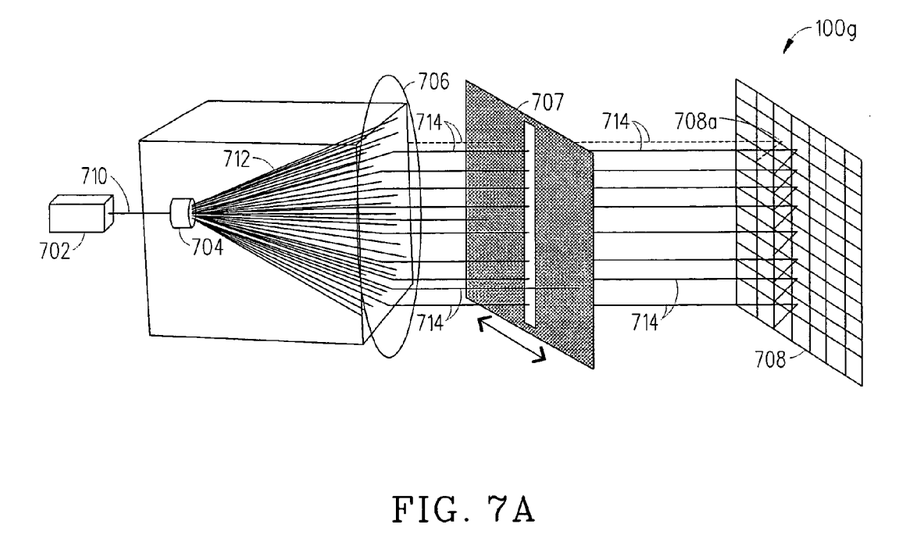
FIG. 7A is a diagram of a seventh embodiment of an optical interrogation system that uses a light source, a diffractive optic, a collimating optic and a movable mask to illuminate predetermined specimens in a specimen array in accordance with the present invention.

Referring to FIG. 7A, there is a diagram of a seventh embodiment of the optical interrogation system 100g. The optical interrogation system 100g is similar to the first embodiment except that this optical interrogation system 100g includes a mask 707 which was not present in the first embodiment. To avoid repetition, the common components between the first and seventh embodiments of the optical interrogation system 100a and 100g such as the light source 102 and 702, the diffractive optic 104 and 704 and the collimating optic 106 and 706 are not described in detail below since each of these components have similar structures and functionalities.

The optical interrogation system 100g includes a light source 702, a diffractive optic 704, a collimating optic 706 and a mask 707 which are used to illuminate predetermined specimens in a specimen array 708. As shown, the light source 702 outputs a light beam 710 towards the diffractive optic 704. The diffractive optic 704 receives the light beam 710 and outputs an array of light beams 712 which have a desired spatial and angular intensity distribution towards the collimating optic 706. The collimating optic 706 receives the light beams 712 and conditions each light beam 712 to have a desired inter-beam separation and angle. The collimating optic 706 then outputs the conditioned light beams 714 some of which pass through the mask 707 towards the specimen array 708. The mask 707 may be coarsely positioned or continuously moving so as to block certain light beams 714 from reaching selected sensors 708a (only one shown) in the specimen array 708. The mask 707 helps to prevent "cross-talk" between sensors in the specimen array 708 and at the detector (see FIGS. 7B–7C). Although the mask 707 is shown placed in the optical path prior to specimen array 708 it could also be placed in the optical path after the specimen array 708. In addition, this masking arrangement allows the use of smaller and/or fewer detectors because the receive optics can direct the signal from more than one specimen in the array 708 to the same location on the detection plane. The mask 707 then blocks the optical signal from specimens that are not being interrogated.

Figure 7B:
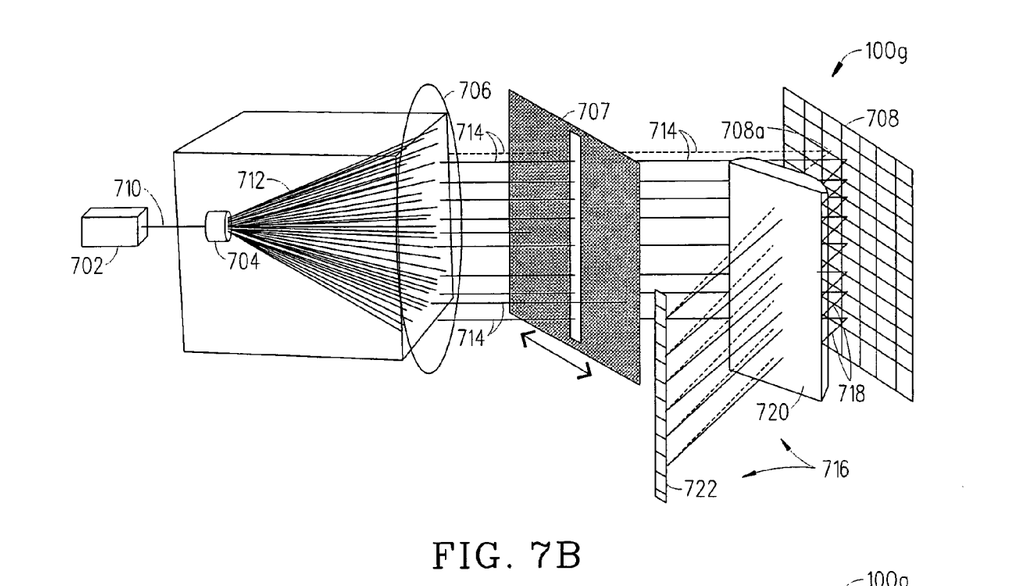
FIG. 7B is a diagram of the optical interrogation system shown in FIG. 7A that includes a detector designed to receive an array of light beams reflected from predetermined specimens in a specimen array in accordance with the present invention.

Referring to FIG. 7B, there is a diagram of the seventh embodiment of the optical interrogation system 100g that includes a detector 716 designed to receive the light beams 718 reflected from the specimen array 708. The detector 716 includes imaging optics 720 which enables the use of 1-D or 2-D arrayed detectors 722 that need fewer detection elements and signal processing components. The imaging optics 720 can be of a cylindrical or spherical design depending on the detection requirements of the particular optical interrogation system 10g. It should be appreciated that this detector 716 and other types of detectors can be used in other embodiments of the present invention.

Figure 7C:
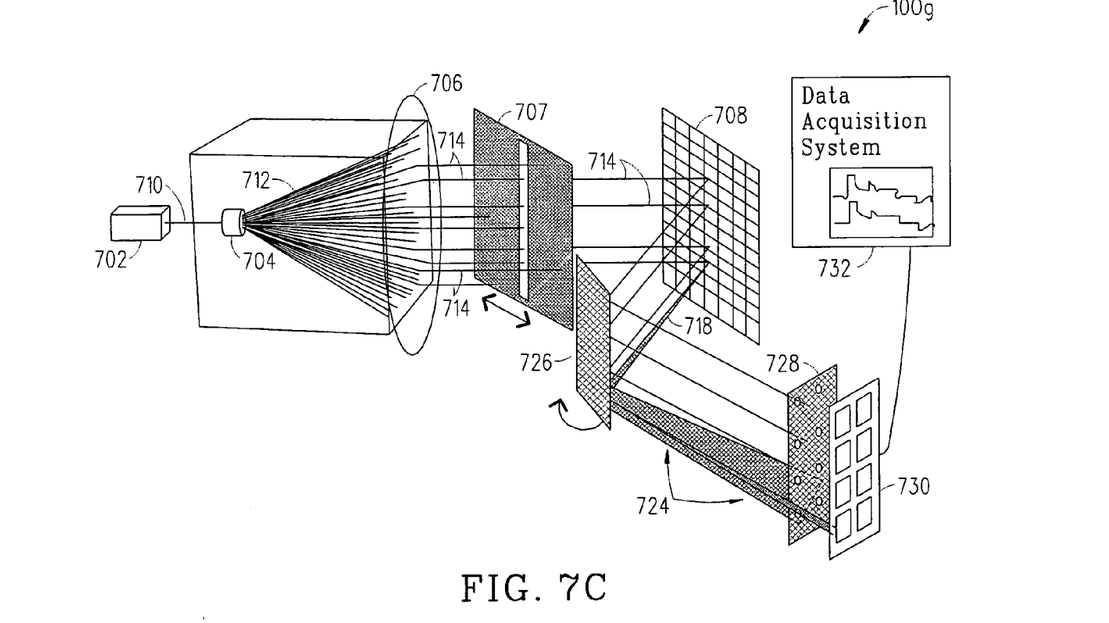
FIG. 7C is a diagram of the optical interrogation system shown in FIG. 7A that includes a swept angle detection system designed to receive an array of light beams reflected from predetermined specimens in a specimen array in accordance with the present invention.

Referring to FIG. 7C, there is a diagram of the seventh embodiment of the optical interrogation system 100g that includes a swept angle detection system 724 designed to receive the light beams 718 reflected from the specimen array 708. The swept angle detection system 724 includes a rotating mirror 726, an aperture array 728, an array of photodetectors 730 and a time/angle based data acquisition system 732. The rotating mirror 726 which moves at a constant velocity or controllable angle receives and reflects the light beams 718 emitted from the specimen array 708. The aperture array 728 shown placed in front of the photodetectors 730 is used to select and pass a small range of angles from the light beams 718 emitted by the specimen array 708 and reflected by the rotating mirror 726. The size of the holes in the aperture array 728 can be changed to improve angular resolution and/or increase the signal strength of the light beams 718. The angular resolutions of the light beams 718 can also be changed by moving the aperture array 728 toward or away from the rotating mirror 726. The light beams 718 passed through the aperture array 728 then interface with the photodetectors 730 which are connected to the data acquisition system 732. It should be noted that the time needed for the data acquisition system 732 to complete a scan can be decreased by increasing the sweep rate of the rotating mirror 726. It should also be noted that a mask 707 may be used to eliminate cross-talk from adjacent sensors in the specimen array 708.

The swept angle detection system 724 enables one to use high gain/high bandwidth detectors 730 and fast time-resolving signal processing hardware that are readily available and supported commercially. Moreover, the swept angle detection system 724 can use a time-resolved method that can be multiplexed electronically using high speed relays to rapidly switch the outputs of the photodetectors 730 to time based signal processing hardware which decreases the cost of the data acquisition system 732. Like the aforementioned detector 716, it should be appreciated that the swept angle detection system 724 and other types of detectors can be used in other embodiments of the present invention.

Figure 8:
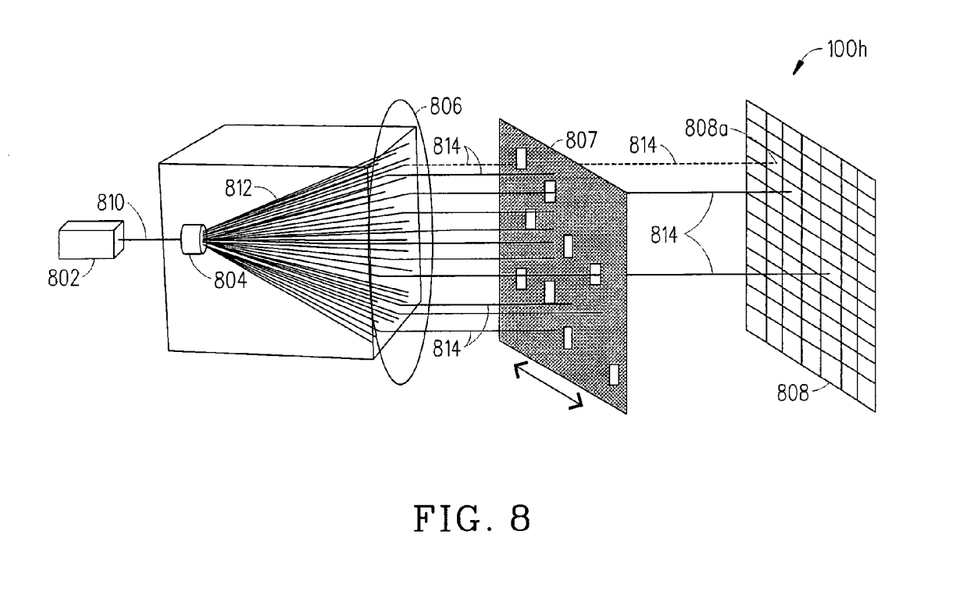
FIG. 8 is a diagram of an eighth embodiment of an optical interrogation system that uses a light source, a diffractive optic, a collimating optic and an electronically controlled liquid crystal mask to illuminate predetermined specimens in a specimen array in accordance with the present invention.

Referring to FIG. 8, there is a diagram of an eighth embodiment of an optical interrogation system 100h. The optical interrogation system 100h is similar to the first embodiment except that this optical interrogation system 100h includes an electronically controlled liquid crystal mask 807 which was not present in the first embodiment. To avoid repetition, the common components between the first and eighth embodiments of the optical interrogation system 100a and 100h such as the light source 102 and 802, the diffractive optic 104 and 804 and the collimating optic 106 and 806 are not described in detail below since each of these components have similar structures and functionalities.

The optical interrogation system 100h includes a light source 802, a diffractive optic 804, a collimating optic 806 and an electronically controlled liquid crystal mask 807 which are used to illuminate predetermined specimens in a specimen array 808. As shown, the light source 802 outputs a light beam 810 towards the diffractive optic 804. The diffractive optic 804 receives the light beam 810 and outputs an array of light beams 812 which have a desired spatial and angular intensity distribution towards the collimating optic 806. The collimating optic 806 receives the light beams 812 and conditions each light beam 812 to have a desired inter-beam separation and angle. The collimating optic 806 then outputs the conditioned light beams 814 some of which pass through the electronically controlled liquid crystal mask 807 towards the specimen array 808. The electronically controlled liquid crystal mask 807 allows one to have selectable control over the transmission or blocking of predetermined light beams 814. In addition, the electronically controlled liquid crystal mask 807 may be coarsely positioned or continuously moving so as to block certain light beams 814 from reaching selected sensors 808a (only one shown) in the specimen array 808. As such, the electronically controlled liquid crystal mask 807 makes it possible to illuminate the desired location or locations on the specimen array 808 at arbitrary times and in controllable spatial patterns. Like mask 707, the electronically controlled liquid crystal mask 807 helps to prevent "cross-talk" between sensors in the specimen array 808 and at the detector (see FIGS. 7B–7C). It should also be appreciated that although the electronically controlled liquid crystal mask 807 is shown placed in the optical path prior to specimen array 708 it could also be placed in the optical path after the specimen array 708.

Figure 9:
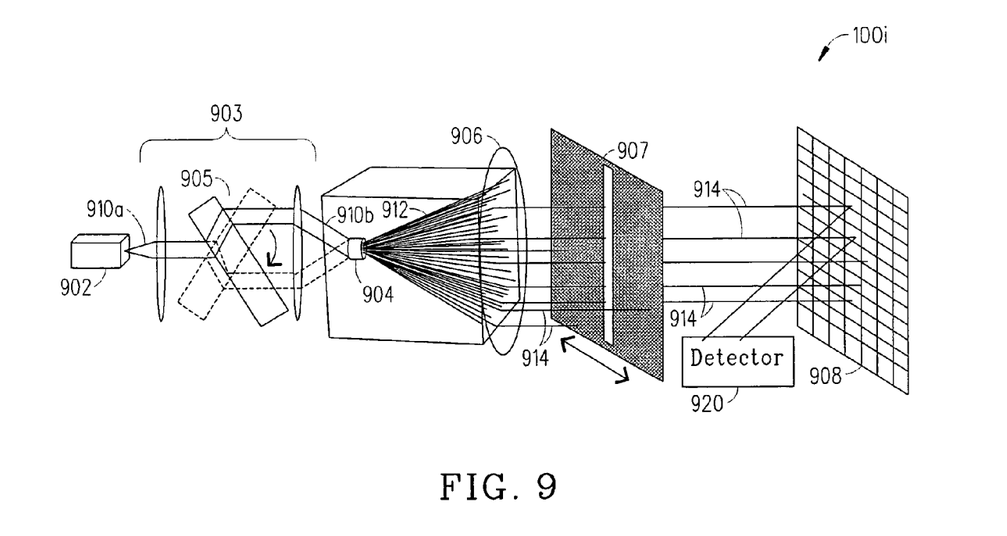
FIG. 9 is a diagram of a ninth embodiment of an optical interrogation system that uses a light source, a swept angle launch system, a diffractive optic, a collimating optic and a mask to illuminate predetermined specimens in a specimen array in accordance with the present invention.

Referring to FIG. 9, there is a diagram of a ninth embodiment of an optical interrogation system 100i. The optical interrogation system 100i is similar to the seventh embodiment except that this optical interrogation system 100i includes a swept angle launch system 903 which was not present in the seventh embodiment (see FIG. 7A). The optical interrogation system 100i includes a light source 902, a swept angle launch system 903, a diffractive optic 904, a collimating optic 906 and a mask 907 which are used to illuminate predetermined specimens in a specimen array 908. As shown, the light source 902 outputs a light beam 910a towards the swept angle launch system 903 which includes a beam deflector 905 used to control the angle of incidence of a light beam 910b directed into the diffractive optic 904. The diffractive optic 904 receives the light beam 910b and outputs an array of light beams 912 which have a desired spatial and angular intensity distribution towards the collimating optic 906. The collimating optic 906 receives the light beams 912 and conditions each light beam 912 to have a desired inter-beam separation and angle. The collimating optic 906 then outputs the conditioned light beams 914 some of which pass through the mask 907 towards the specimen array 708. The mask 907 may be the same as the aforementioned masks 707 and 807 described above with respect to FIGS. 7A and 8.

The swept angle launch system 903 has several features and advantages including the following (for example):

Enables one to perform measurements on signals which are sensitive to the angle of incidence and/or the angle of deflection of light.

Enables one to use a large area detector 920 instead of the more expensive CCD which is really an array of detectors. This is possible because one knows the angles of incidence of the light beams 914 that are impinging on the sensors in the specimen array 907 for each measurement point in the angular sweep.

Enables one to incorporate phase sensitive detection/locking techniques within the optical interrogation systems 100i which can greatly reduce noise and boost by orders of magnitude the signal sensitivity.

Enables one to address a fringe problem at the detector 920 that occurs when light beams that have a large range of angles and/or large spot sizes impinge simultaneously at one of the sensors in the specimen array 908. These problematical fringes are the result of the interference of the light beams caused by reflections from the sensor 908 to detector 920. As the range of incident angles of the light beams that arrive at the sensor 908 are simultaneously reduced, so are the number of fringes observed at the detector 920. Thus, if the light beams have a small enough range of incidence angles, then the reflections from both surfaces on the sensor namely the bottom of the well and the sensor itself do not overlap at the detector which causes the fringe problem. The swept angle launch system 903 reduces most of the undesirable interference fringe effect by reducing the range of the incident angles of light beams that impinge the sensor 908. In addition, at the same time, the swept angle launch system 903 enables one to cover the full range of angles needed to maintain the angular dynamic range of the measurement by sweeping the angle of the light beam across the sensor 908.

Figure 10:
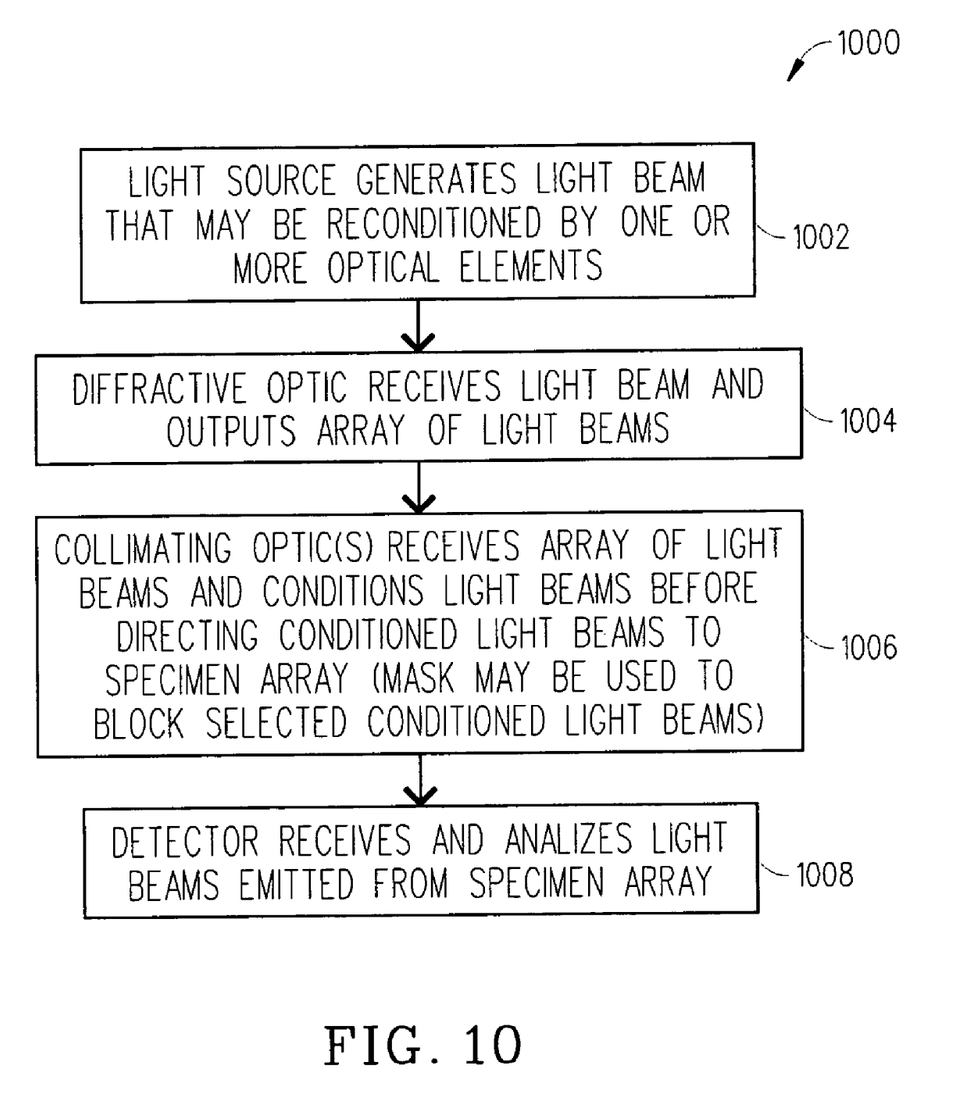
FIG. 10 is a flowchart illustrating the basic steps of a preferred method for interrogating one or more specimens in a specimen array using the aforementioned optical interrogation systems in accordance with the present invention.

Referring to FIG. 10, there is a flowchart illustrating the basic steps of a preferred method 1000 for interrogating one or more specimens in a specimen array using the aforementioned optical interrogation systems 100. Beginning at step 1002, a light source 102 is used to generate a light beam 110 that may be reconditioned by one or more optical elements.

At step 1004, a diffractive optic 104 is used to receive the light beam 110 and output an array of light beams 112. At step 1006, a collimating optic 106 (e.g., simple lens(es), f-θ lens(es), segmented mirror, fiber array) is used to receive and condition the array of light beams 112 and then output the conditioned array of light beams 114 which have desired optical properties towards the specimen array 107. A mask 708 and 807 may also be used to prevent certain light beams 114 from reaching certain specimens in the specimen array 107. Lastly at step 1008, a detector is used to receive and analyze the light beams 114 emitted from the specimen array 107. Although this method 1000 has been described with respect to the components associated with the first embodiment of the optical interrogation system 100a the basic steps are applicable to any of the aforementioned embodiments of optical interrogation systems.

Following are some advantages and uses of the optical interrogation system 100 and method 1000 of the present invention:

The optical interrogation system 100 provides a simple and efficient means of generating an array of beams with precisely controlled spacing and optical characteristics at the specimen array.

The optical interrogation system 100 has a minimum number of or no moving parts.

The optical interrogation system 100 does not require precise movement or alignment of its components to optically interrogate rows and/or individual sensors in the specimen array.

The optical interrogation system 100 allows a large number of specimens to be interrogated simultaneously.

The optical interrogation system 100 could be applied in the following applications (for example):

Grating and non-grating based sensors.

Infrared and Ultra-violet Absorption Spectroscopy, Fourier Transform Infrared Absorption (FTIR) Spectroscopy, Raman Spectroscopy, Reflection Spectroscopy, Fluorescence Spectroscopy, Flourescence Lifetime Spectroscopy, and Surface Plasmon Resonance Spectroscopy.

The optical interrogation system 100 can have optical frequencies that span across the entire usable electromagnetic frequency spectrum.

Although several embodiments of the present invention has been illustrated in the accompanying Drawings and described in the foregoing Detailed Description, it should be understood that the invention is not limited to the embodiments disclosed, but is capable of numerous rearrangements, modifications and substitutions without departing from the spirit of the invention as set forth and defined by the following claims.

What is claimed is:

1. An optical interrogation system comprising:

a light source for outputting a light beams;

a diffractive optic for receiving the light beam and outputting an array of light beams;

a collimating optic for receiving and conditioning the array of light beams and outputting the conditioned array of light beams which have desired optical properties towards a specimen array;

wherein said collimating optic is a fiber array that reconditions the optical character of each light beam emitted from said diffractive optic; and wherein said fiber array includes a plurality of fibers each of which has one end arranged on a circumference of a sphere and another end connected to a grid.

2. The optical interrogation system of claim 1, further comprising a detector for receiving an array of light beams reflected from the specimen array.

3. The optical interrogation system of claim 1, further comprising a beam reconditioning optic located between said light source and said diffractive optic and used for controlling the numerical aperture, spot size, and angle of incidence of each light beam emitted from said collimating optic that impinges a plane of the specimen array.

4. The optical interrogation system of claim 1, further comprising a wavelength tunable filter located between said light source and said diffractive optic and used to adjust each light beam emitted from said collimating optic to enable wavelength interrogation of the specimen array.

5. The optical interrogation system of claim 1 is used to interrogate grating or non-grating based sensors in a specimen array.

6. The optical interrogation system of claim 1 is used in one of the following applications including Infrared and Ultra-violet Absorption Spectroscopy, Fourier Transform Infrared Absorption (FTIR) Spectroscopy, Raman Spectroscopy, Reflection Spectroscopy, Fluorescence Spectroscopy, Flourescence Lifetime Spectroscopy or Surface Plasmon Resonance Spectroscopy.

7. The optical interrogation system of claim 1 has optical frequencies that span across the entire usable electromagnetic frequency spectrum.

8. An optical interrogation system comprising:
a light source for outputting a light beam;
a diffractive optic for receiving the light beam and outputting an array of light beams;
a collimating optic for receiving and conditioning the array of light beams and outputting the conditioned array of light beams which have desired optical properties towards a specimen array; and
a mask located between said collimating optic and said specimen array and used to block predetermined conditioned light beams from reaching selected specimens in the specimen array.

9. The optical interrogation system of claim 8, wherein said mask is an electronically controlled liquid crystal mask.

10. The optical interrogation system of claim 8, wherein said collimating optic is a simple lens, array of simple lenses, f-θ lens, parabolic mirror, segmented mirror, or a refracting lens made from a set of precisely placed and angled refracting wedges.

11. The optical interrogation system of claim 8, wherein said collimating optic is a segmented mirror and each segment of said segmented mirror reflects one of the light beam is emitted from said diffractive optic so that the reflected light beam is equidistant from neighboring reflected light beams when impinging a plane of the specimen array.

12. The optical interrogation system of claim 8, wherein said collimating optic is a lenslet array that re-conditions the optical character of each light beam emitted from said diffractive optic.

13. The optical interrogation system of claim 8, wherein said collimating optic is a fiber array that re-conditions the optical character of each light beam emitted from said diffractive optic.

14. The optical interrogation system of claim 8, wherein said collimating optic is a combined fiber array and lenslet array that re-conditions the optical character of each light beam emitted from said diffractive optic.

15. An optical interrogation system comprising:
a light source for outputting a light beam;
a diffractive optic for receiving the light beam and outputting an array of light beams;
a collimating optic for receiving and conditioning the array of light beams and outputting the conditioned array of light beams which have desired optical properties towards a specimen array; and
a mask located between a detector and said specimen array and used to block predetermined light beams reflected from selected specimens in the specimen array.

16. The optical interrogation system of claim 15, wherein said mask is an electronically controlled liquid crystal mask.

17. The optical interrogation system of claim 15, wherein said collimating optic is a simple lens, array of simple lenses, f-θ lens, parabolic mirror, segmented mirror, or a refracting lens made from a set of precisely placed and angled refracting wedges.

18. The optical interrogation system of claim 15, wherein said collimating optic is a segmented mirror and each segment of said segmented mirror reflects one of the light beams emitted from said diffractive optic so that the reflected light beam is equidistant from neighboring reflected light beams when impinging a plane of the specimen array.

19. The optical interrogation system of claim 15, wherein said collimating optic is a lenslet array that re-conditions the optical character of each light beam emitted from said diffractive optic.

20. The optical interrogation system of claim 15, wherein said collimating optic is a fiber array that re-conditions the optical character of each light beam emitted from said diffractive optic.

21. The optical interrogation system of claim 15, wherein said collimating optic is a combined fiber array and lenslet array that re-conditions the optical character of each light beam emitted from said diffractive optic.

22. An optical interrogation system comprising:
a light source for outputting a light beam;
a diffractive optic for receiving the light beam and outputting an array of light beams;
a collimating optic for receiving and conditioning the array of light beams and outputting the conditioned array of light beams which have desired optical properties towards a specimen array; and
a swept angle detection system for receiving an array of light beams reflected from the specimen array.

23. The optical interrogation system of claim 15, wherein said swept angle detection system includes:
a rotating mirror for reflecting an array of light beams reflected from the specimen array;
an aperture plate having one or more holes through which passes selected ones of the light beams reflected from the rotating mirror;
an array of photodetectors for receiving the light beams that passed through the aperture plate; and
a data acquisition system for analyzing data received from said array of photodetectors.

24. An optical interrogation system comprising:
a light source for outputting a light beam;
a diffractive optic for receiving the light beam and outputting an array of light beams;
a collimating optic for receiving and conditioning the array of light beams and outputting the conditioned array of light beams which have desired optical properties towards a specimen array; and a swept angle launch system including a rotatable beam deflector located between said light source and said diffractive optic to control the angle of incidence of the light beam directed into said diffractive optic.

25. A method for interrogating one or more specimens in a specimen array, said method comprising the steps of:
using a light source to generate a light beam;
using a diffractive optic to receive the light beam and output an array of light beams;
using a collimating optic to receive and condition the array of light beams and then output the conditioned array of light beams which have desired optical properties towards a specimen array;
wherein said collimating optic is a fiber array that re-conditions the optical character of each light beam emitted from said diffractive optic; and
wherein said fiber array includes a plurality of fibers each of which has one end arranged on a circumference of a sphere and another end connected to a grid.

26. The method of claim 25, further comprising the step of using a detector to receive an array of light beams reflected from the specimen array.

27. The method of claim 25, further comprising the step of using a beam reconditioning optic located between said light source and said diffractive optic to control the numerical aperture, spot size, and angle of incidence of each light beam emitted from said collimating optic that impinges a plane of the specimen array.

28. The method of claim 25, further comprising the step of using a wavelength tunable filter located between said light source and said diffractive optic to adjust each light beam emitted from said collimating optic to enable wavelength interrogation of the specimen array.

29. A method for interrogating one or more specimens in a specimen array, said method comprising the steps of:
using a light source to generate a light beam;
using a diffractive optic to receive the light beam and output an array of light beams; and
using a collimating optic to receive and condition the array of light beams and then output the conditioned array of light beams which have desired optical properties towards a specimen array; and
using a mask located between said collimating optic and said specimen array to block predetermined conditioned light beams from reaching selected specimens in the specimen array.

30. The method of claim 29, wherein said mask is an electronically controlled liquid crystal mask.

31. The method of claim 29, wherein said collimating optic is a simple lens, array of simple lenses, f-θ lens, parabolic mirror, segmented mirror, or a refracting lens made from a set of precisely placed and angled refracting wedges.

32. The method of claim 29, wherein said collimating optic is a segmented mirror and each segment of said segmented mirror reflects one of the light beams emitted from said diffractive optic so that the reflected light beam is equidistant from neighboring reflected light beams when impinging a plane of the specimen array.

33. The method of claim 29, wherein said collimating optic is a lenslet array that re-conditions the optical character of each light beam emitted from said diffractive optic.

34. The method of claim 29, wherein said collimating optic is a fiber array that re-conditions the optical character of each light beam emitted from said diffractive optic.

35. The method of claim 29, wherein said collimating optic is a combined fiber array and lenslet array that re-conditions the optical character of each light beam emitted from said diffractive optic.

36. A method for interrogating one or more specimens in a specimen array, said method comprising the steps of:
using a light source to generate a light beam;
using a diffractive optic to receive the light beam and output an array of light beams; and
using a collimating optic to receive and condition the array of light beams and then output the conditioned array of light beams which have desired optical properties towards a specimen array; and
using a mask located between a detector and said specimen array to block predetermined light beams reflected from selected specimens in the specimen array.

37. The method of claim 36, wherein said mask is an electronically controlled liquid crystal mask.

38. The method of claim 36, wherein said collimating optic is a simple lens, array of simple lenses, f-θ lens, parabolic mirror, segmented mirror, or a refracting lens made from a set of precisely placed and angled refracting wedges.

39. The method of claim 36, wherein said collimating optic is a segmented mirror and each segment of said segmented mirror reflects one of the light beams emitted from said diffractive optic so that the reflected light beam is equidistant from neighboring reflected light beams when impinging a plane of the specimen array.

40. The method of claim 36, wherein said collimating optic is a lenslet array that re-conditions the optical character of each light beam emitted from said diffractive optic.

41. The method of claim 36, wherein said collimating optic is a fiber array that re-conditions the optical character of each light beam emitted from said diffractive optic.

42. The method of claim 36, wherein said collimating optic is a combined fiber array and lenslet array that re-conditions the optical character of each light beam emitted from said diffractive optic.

43. A method for interrogating one or more specimens in a specimen array, said method comprising the steps of:
using a light source to generate a light beam;
using a diffractive optic to receive the light beam and output an array of light beams;
using a collimating optic to receive and condition the array of light beams and then output the conditioned array of light beams which have desired optical properties towards a specimen array; and
using a swept angle detection system to receive an array of light beams reflected from the specimen array.

44. The method of claim 43, wherein said swept angle detection system includes:
a rotating mirror for reflecting an array of light beams reflected from the specimen array;
an aperture plate having one or more holes through which passes selected ones of the light beams reflected from the rotating mirror;
an array of photodetectors for receiving the light beams that passed through the aperture plate; and
a data acquisition system for analyzing data received from said array of photodetectors.

45. A method for interrogating one or more specimens in a specimen array, said method comprising the steps of:

using a light source to generate a light beam;

using a diffractive optic to receive the light beam and output an array of light beams;

using a collimating optic to receive and condition the array of light beams and then output the conditioned array of light beams which have desired optical properties towards a specimen array; and using a swept angle launch system including a rotatable or acousto-optical beam deflector located between said light source and said diffractive optic to control the angle of incidence of the light beam directed into said diffractive optic.

* * * * *